United States Patent
Wang et al.

(10) Patent No.: US 12,258,656 B2
(45) Date of Patent: Mar. 25, 2025

(54) IN-SITU MAGNESIUM HYDROXIDE NANOSHEET LAYER MODIFIED MAGNESIUM ALLOY AND PREPARATION AND APPLICATION THEREOF

(71) Applicant: SHENZHEN INSTITUTES OF ADVANCED TECHNOLOGY CHINESE ACADEMY OF SCIENCES, Guangdong (CN)

(72) Inventors: Guomin Wang, Guangdong (CN); Huaiyu Wang, Guangdong (CN); Kimho Paul Chu, Guangdong (CN)

(73) Assignee: SHENZHEN INSTITUTES OF ADVANCED TECHNOLOGY CHINESE ACADEMY OF SCIENCES, Guangdong (CN)

( * ) Notice: Subject to any disclaimer, the term of this patent is extended or adjusted under 35 U.S.C. 154(b) by 581 days.

(21) Appl. No.: 16/624,542

(22) PCT Filed: Sep. 30, 2019

(86) PCT No.: PCT/CN2019/109475
§ 371 (c)(1),
(2) Date: Oct. 6, 2021

(87) PCT Pub. No.: WO2021/035875
PCT Pub. Date: Mar. 4, 2021

(65) Prior Publication Data
US 2022/0090236 A1 Mar. 24, 2022

(30) Foreign Application Priority Data
Aug. 30, 2019 (CN) .......................... 201910818027.4

(51) Int. Cl.
C23C 22/60 (2006.01)
A61L 27/04 (2006.01)
(Continued)

(52) U.S. Cl.
CPC ............ *C22C 23/00* (2013.01); *A61L 27/047* (2013.01); *A61L 27/306* (2013.01); *A61L 27/54* (2013.01);
(Continued)

(58) Field of Classification Search
CPC ......... A61L 2300/102; A61L 2300/404; A61L 2300/606; A61L 2400/12; A61L 2400/18;
(Continued)

(56) References Cited

FOREIGN PATENT DOCUMENTS

CN 103614717 A * 3/2014
CN 106567062 B * 3/2019

OTHER PUBLICATIONS

NPL: on-line translation of CN-106567062-B, Mar. 2019 (Year: 2019).*
(Continued)

*Primary Examiner* — Jie Yang
(74) *Attorney, Agent, or Firm* — Renner, Otto, Boisselle & Sklar, LLP (57) ABSTRACT

The present invention relates to a magnesium alloy material, which is an in situ magnesium hydroxide nanosheet layer modified magnesium alloy. The material is prepared from a magnesium alloy through a hydrothermal reaction under alkaline condition. The protective effect of the in situ formed magnesium hydroxide nanosheet layer structure results in remarkably enhanced corrosion resistance of the magnesium alloy, meanwhile the biocompatibility can also be significantly improved since the release rate of magnesium ion can be significantly reduced. In addition, the two-dimensional nanolayer structure has a non-releasing physical antibacterial property depending on contact. Therefore, the magnesium alloy material according to the present invention has an extremely great application prospect in the field of medical implant.

10 Claims, 12 Drawing Sheets

(51) Int. Cl.
  *A61L 27/30* (2006.01)
  *A61L 27/54* (2006.01)
  *C22C 23/00* (2006.01)
  *B82Y 5/00* (2011.01)

(52) U.S. Cl.
  CPC ......... *C23C 22/60* (2013.01); *A61L 2300/404* (2013.01); *A61L 2400/18* (2013.01); *A61L 2420/02* (2013.01); *B82Y 5/00* (2013.01)

(58) Field of Classification Search
  CPC .. A61L 2420/02; A61L 27/047; A61L 27/306; A61L 27/50; A61L 27/54; B82Y 5/00; C22C 23/00; C23C 22/60
  See application file for complete search history.

(56) References Cited

OTHER PUBLICATIONS

NPL: on-line translation of CN-103614717-A, Mar. 2014 (Year: 2014).*
NPL: Sheng et al, Microstructure and Mechanical Properties of AZ31 Mg Alloy Fabricated by Pre-compression and Frustum Shearing Extrusion. Acta Metallurgica Sinica (English Letters) (2019) 32 pp. 235-244, (Year: 2019).*

* cited by examiner

IN-SITU MAGNESIUM HYDROXIDE NANOSHEET LAYER MODIFIED MAGNESIUM ALLOY AND PREPARATION AND APPLICATION THEREOF

REFERENCE TO RELATED APPLICATION

This application is the United States National Stage entry under 35 U.S.C. 371 of PCT/CN2019/109475 filed on Sep. 30, 2019, which in turn claims the priority of Chinese patent application no. 201910818027.4 entitled "AN IN-SITU MAGNESIUM HYDROXIDE NANOSHEET LAYER MODIFIED MAGNESIUM ALLOY AND PREPARATION AND APPLICATION THEREOF" filed on Aug. 30, 2019, both of which are hereby incorporated by reference in their entirety.

FIELD OF THE INVENTION

The present invention relates to a surface modified magnesium alloy, in particular to an in-situ magnesium hydroxide nanosheet layer modified magnesium alloy and preparation and application thereof.

BACKGROUND OF THE INVENTION

Magnesium alloy is one of the green engineering materials in the $21^{st}$ century, and has great application prospects in the fields of aerospace, transportation, 3C products, biomedicine, national defense industry, and marine engineering, and the like. Since 2013, there have been many related research papers published in the top grade journals such as *Nature, Science, Nature Materials, Nature Medicine*, and *Nature Communications*. The research and development and processing of novel magnesium alloys is one of the frontier hotspots in the research of metal materials nowadays. Magnesium and magnesium alloys have attracted attentions in the medical field and are intended to be used as degradable implant materials due to their biodegradability and absorbability. However, the metal of magnesium degrades too quickly in the body and thus affects the tissue recovery. Therefore, a surface treatment method is usually used to reduce the degradation rate. An unmodified magnesium alloy has an antibacterial effect based on release of magnesium ions and an alkaline microenvironment, and anti-corrosion modification of the surface tends to greatly reduce the antibacterial effect of the magnesium alloy itself. Therefore, trying to find an anti-corrosion modification method that maintains the antibacterial effect and enhances the biocompatibility is of great significance for the biomedical applications of magnesium alloys.

Previous studies have shown that the magnesium alloy itself has an antibacterial effect based on release of magnesium ions and increase in pH value, which belongs to a release-type sterilization process. In fact, the release-type antibacterial mechanism comprising antibiotic-dependent grafting and release of antibacterial molecule or ion has always been the mainstream mechanism. Although it can effectively control the bacterial infection, high concentration of antibacterial agents and uncontrollable drug release may cause the bacterial resistant to drug and then cause various side effects. Therefore, when designing a bone articular implant, the surface design that relies on contact for the antibacterial activity in the surrounding microenvironment will better avoid the systemic side effects as described above.

SUMMARY OF THE INVENTION

In view of the above status, the present invention aims to form a two-dimensional nano-layer structure on the surface of the magnesium alloy in situ by hydrothermal treatment, this structure has relatively strong binding force with the substrate to ensure the stability of the material, and the protective effect of this structure results in remarkably enhanced corrosion resistance of the magnesium alloy, and significantly improved biocompatibility since the release rate of magnesium ions can be significantly reduced. In addition, the two-dimensional nanolayer structure has a non-releasing physical antibacterial property depending on contact at the early stage of implantation. Contact of the nanosheet layer with bacteria can exert a tangential force on the bacterial surface, tearing the bacterial film and causing mechanical stress to inactivate the bacteria.

Specifically, the present invention comprises three parts. First, a hydrothermal method is used to form a two-dimensional nanosheet layer in situ on the surface of the magnesium alloy, then the material is verified for the improvement of its antibacterial property, anticorrosion property, and in vitro biocompatibility, meanwhile the antibacterial mechanism is explained from both the experimental and simulational calculation levels. Finally, an animal infection model is designed to verify its feasibility as an implant material.

The present invention firstly provides a magnesium alloy material comprising a magnesium alloy body and a magnesium hydroxide nanosheet layer on the surface; the magnesium hydroxide nanosheet in the magnesium hydroxide nanosheet layer has an area between 1 $nm^2$ and 10 $\mu m^2$ and a thickness between 1 nm and 2 $\mu m$.

Preferably, the magnesium hydroxide nanosheet has an area between 50 $nm^2$ and 5 $\mu m^2$, more preferably between 100 $nm^2$ and 2 $\mu m^2$; and most preferably between 200 $nm^2$ and 1 $\mu m^2$.

Preferably, the magnesium hydroxide nanosheet has a thickness between 5 nm and 1 $\mu m$, more preferably between 10 and 800 nm; and most preferably between 20 and 600 nm.

Preferably, the magnesium alloy body is a magnesium alloy having a magnesium content greater than 85%; preferably a magnesium content greater than 90%; more preferably greater than 92%; and most preferably greater than 95%.

According to the present invention, there is also provided a preparation method of the above magnesium alloy materials, comprising the step of conducting a hydrothermal reaction of the magnesium alloy under an alkaline condition to form a magnesium hydroxide nanosheet layer in situ.

Preferably, the temperature of the above hydrothermal reaction is from 60 to 200° C.; and the reaction time is more than 30 minutes.

The temperature of the hydrothermal reaction is more preferably from 80 to 180° C., and most preferably from 90 to 160° C.;

The reaction time of the hydrothermal reaction is preferably greater than 2 hours; more preferably greater than 4 hours; and most preferably 8 to 72 hours.

The heating rate of the hydrothermal reaction is preferably from 1 to 30° C. $min^{-1}$; more preferably from 2 to 20° C. $min^{-1}$; and most preferably from 5 to 15° C. $min^{-1}$.

The alkaline condition for the hydrothermal reaction refers to a pH value between 8 and 14, and preferably from 8 to 12.

Preferably, the pH value of the hydrothermal reaction is controlled using an aqueous solution of sodium hydroxide, potassium hydroxide, calcium hydroxide, barium hydroxide or aqueous ammonia.

Preferably, according to the present invention, the step of grinding, polishing and cleaning of the magnesium alloy is also included prior to the hydrothermal reaction.

Preferably, the magnesium alloy after grinding and polishing is washed using alcohol.

Preferably, according to the present invention, a step of cleaning the magnesium alloy material after the hydrothermal reaction is further included.

Preferably, the cleaning is alcohol washing.

More preferably, the alcohol washing is performed under ultrasound.

The alcohol in the above alcohol washing is preferably 75% or more alcohol; more preferably 90% or more alcohol; and most preferably industrially pure or of a higher grade.

The present invention also relates to the use of the above-described magnesium alloy materials in medical implants.

According to the present invention, the anticorrosion property, antibacterial property, and biocompatibility of the magnesium alloy materials are also investigated.

Wherein, the solution for the corrosion resistance test may be bacterial culture medium, simulated artificial body fluid or water.

Methods for testing corrosion resistance include electrochemical workstation test method and immersing and weighing method. The cells used in the in vitro experiments for testing biocompatibility may be osteoblast or other normal cells.

The bacteria used for testing of the antibacterial effect may be any bacteria, preferably Gram-positive or Gram-negative bacteria; and most preferably *Staphylococcus aureus* and *Escherichia coli*.

The concentration of bacteria used for antibacterial property testing is $10$-$10^6$ CFU mL$^{-1}$.

In the antibacterial test, the material is allowed to interact with the bacteria for a certain period of time, preferably 0 to 24 h.

The method for testing the in vitro antibacterial effect is not particularly limited, and conventional methods comprising spread plate method, biofilm inhibition detection method, fluorescence detection method, and flow cytometry detection method can be used.

Experimental methods for antibacterial mechanism study include, but are not limited to, live-dead bacterial staining, detection of bacterial internal and external reactive oxygen, and physicochemical property test of extracellular media comprising release of magnesium ion, pH, and ORP test.

According to the present invention, in order to further investigate the antibacterial property of the materials, evaluations are also made by in vivo experiments, including comparison of the number of colonies from the implant and from surrounding tissues, and the inflammatory response of the surrounding tissues.

In a narrow sense, it has been confirmed by the above performance studies that the present invention utilizes a hydrothermal film containing nanosheet to achieve the unification of corrosion resistance and sterilization of the surface of a medical magnesium alloy, and a hydrothermal method is used to construct a layer of magnesium hydroxide nanosheet on the surface of the magnesium alloy. The nanosheet can enhance the corrosion resistance effect by reducing the corrosion rate of the substrate, and the biocompatibility is significantly improved based on decrease in the release rate of ions. In addition, the nanosheet can achieve excellent antibacterial effect by means of mechanical force on bacteria. It is a major breakthrough on technical level. In a broad sense, the non-release type antibacterial mechanism proposed by the present invention has guiding significance for design of biomaterials with local antibacterial requirement.

Compared with conventional surface modified magnesium alloys, the present invention has the following advantages:

1. By adjusting the reaction solution to a specific pH value, a two-dimensional magnesium hydroxide sheet layer can be formed in situ on the surface of the magnesium alloy by reaction at a specific temperature for a certain period of time, without needs of introducing other substances, and in-situ growth can ensure the binding force between the coating and the substrate.
2. Conventional magnesium alloy modification methods tend to focus on reducing the corrosion rate, but the preparation of the two-dimensional nanosheet in the present invention can enable the integration of the corrosion resistance, improved biocompatibility and antibacterial effect of the magnesium alloy, which is closer to clinical application.
3. The present invention is a non-release type antibacterial process, rather than a release type antibacterial process inhibiting the magnesium alloy itself, and the antibacterial system of the present invention is a local antibacterial system which relies on contact with bacteria and can accurately kill bacteria in the vicinity of the implanting operation wound compared with the antibacterial surface which releases ion or drug, thereby achieving high anti-infection efficiency.
4. Unlike the bioactive materials such as antibacterial peptides, this material avoids hidden safety risks.
5. Drug resistance is avoided compared to the antibacterial modification that relies on antibiotic grafting.
6. The sterilization mechanism of this antibacterial system is based on the mechanical action between the material and the bacteria, and is simpler and cleaner than the previous sterilization mechanism of the drug release surface.
7. The design process of the material is simple, the technology is mature, and it is suitable for mass production.
8. The present invention will not cause a change in the biocompatibility of the magnesium alloy, ensuring its safety when applied into human body.

BRIEF DESCRIPTION OF THE DRAWINGS

FIGS. 15*a-e* show the results wherein

DETAILED DESCRIPTION OF THE EMBODIMENTS

Example 1

Figure 1:
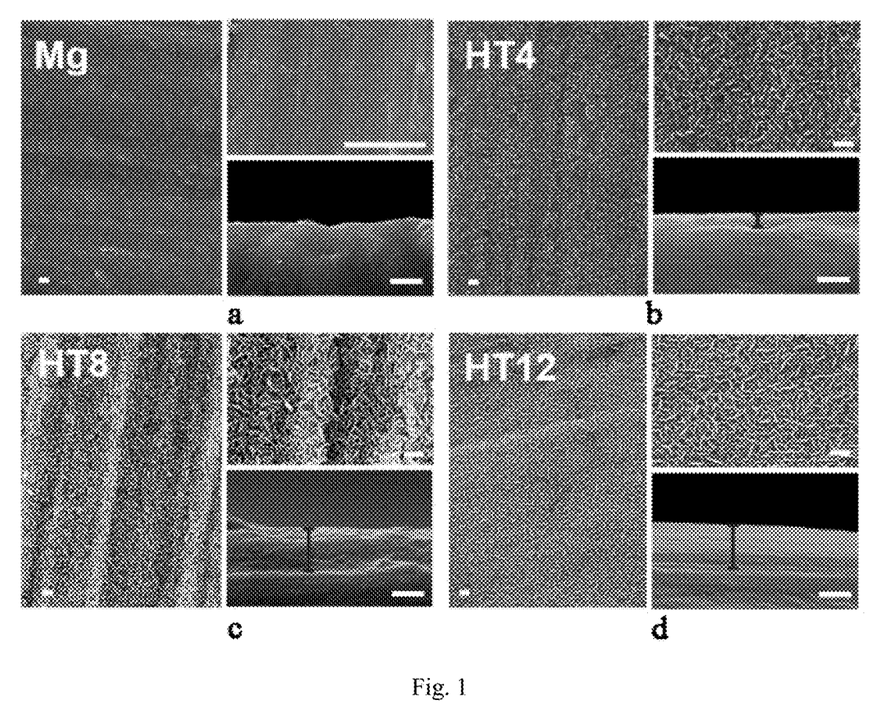
FIG. 1 shows the micromorphologies of the surface and cross-section after 12 hours of hydrothermal treatment under a scanning electron microscope (scale=1 μm); wherein, a represents the untreated magnesium alloy (Mg); b represents the magnesium alloy after 4 hours of hydrothermal treatment (HT4); c represents the magnesium alloy after 8 hours of hydrothermal treatment (HT8); and d represents the magnesium alloy after 12 hours of hydrothermal treatment (HT12).

Magnesium sheets with a length×width×height of 10 mm×10 mm×5 mm were polished and grinded, and washed well with alcohol. The samples were placed into a reaction kettle with a volume of 25 mL, and 10 mL of aqueous sodium hydroxide solution of pH=12 was added. The reaction kettle was screwed and placed in a muffle furnace, wherein the heating rate was 10° C. min$^{-1}$, the reaction temperature was 120° C., and the reaction time was 4 h, 8 h and 12 h. After the reaction was completed, the micromorphologies of various samples were observed by scanning electron microscope respectively. As can be seen in FIG. 1, a magnesium hydroxide micro-nanosheet layer with a surface area of 1 μm$^2$ and a thickness of 5 nm was formed on the surface of the magnesium alloy after 12 h of hydrothermal reaction.

Example 2

Figure 2:
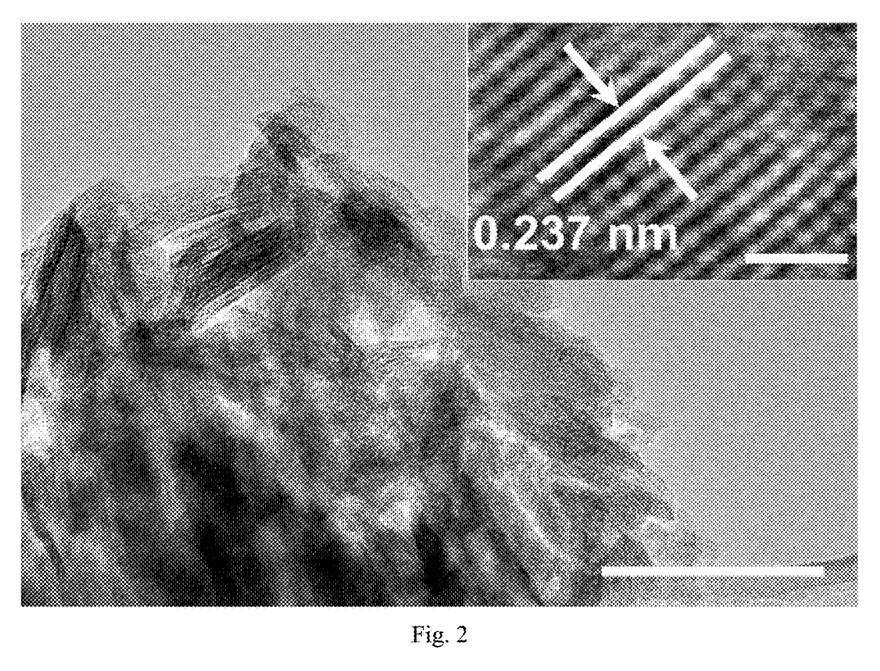
FIG. 2 shows the morphology and crystal form of HT12 by a high-resolution transmission scanning electron microscopy analysis (scale=100 nm; scale of the partial enlarged view=2 nm).
Figure 3:
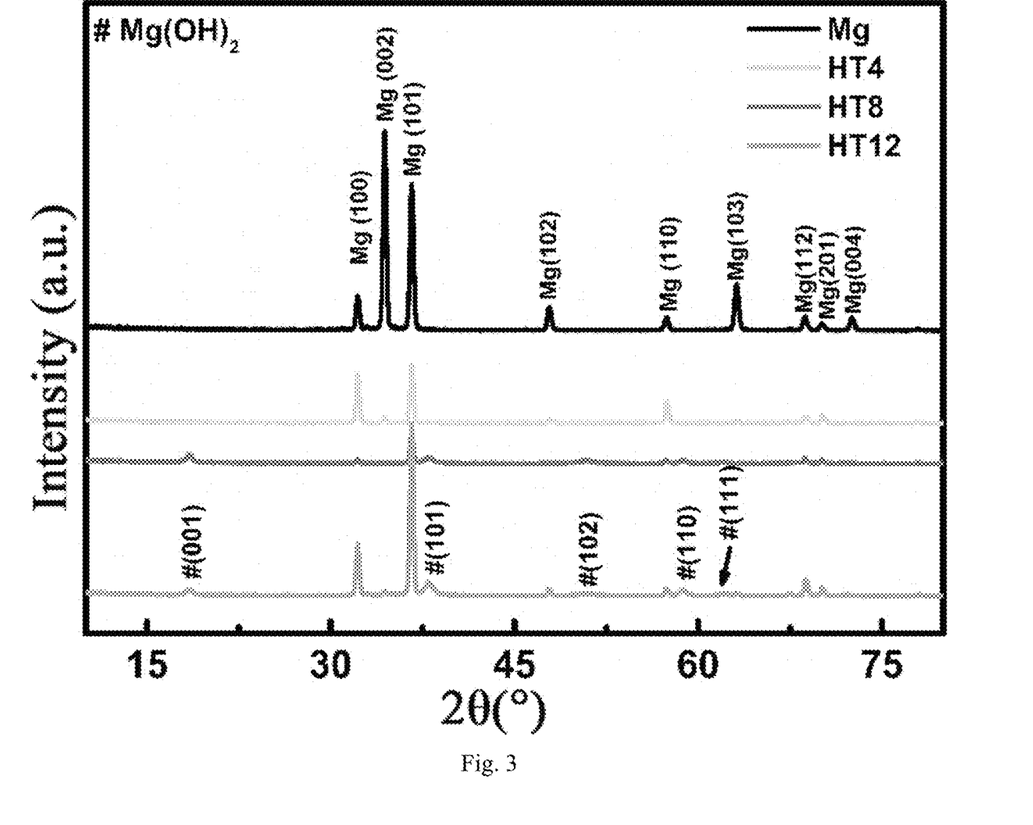
FIG. 3 shows the comparison of XRD patterns of various samples.
Figure 4:
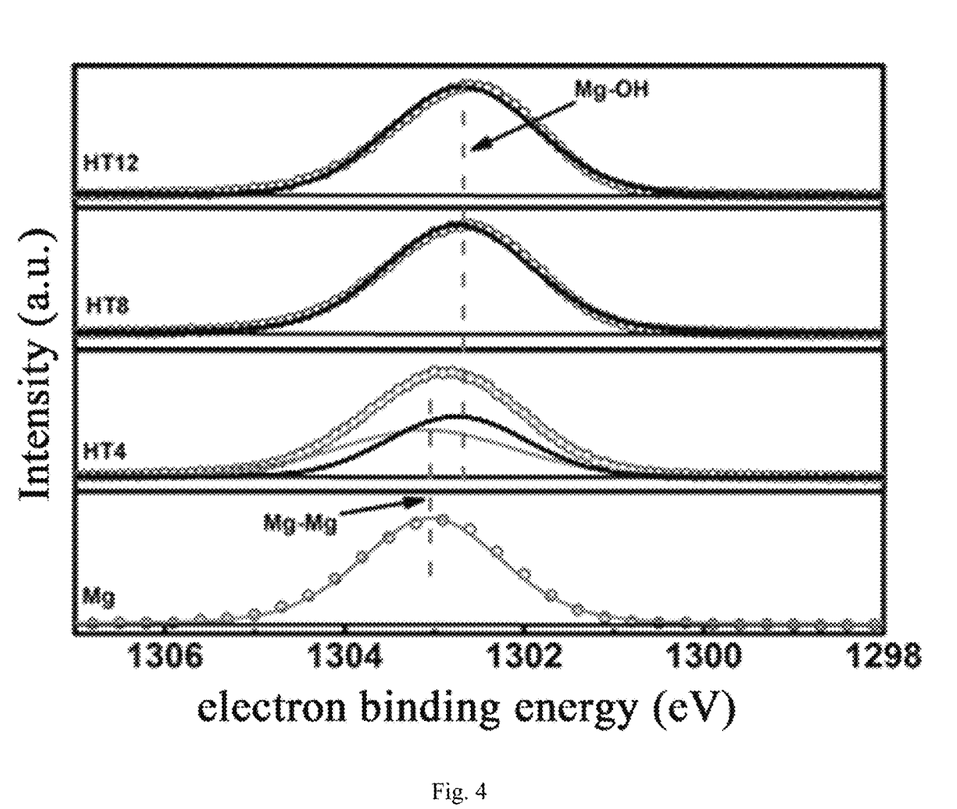
FIG. 4 shows the Mg 1 s spectrum in high resolution XPS.

The surfaces of the samples obtained by the treatment of Example 1 were subjected to crystallography and chemical element analysis. The results from high resolution TEM (FIG. 2) showed that HT12 had a magnesium hydroxide crystal form with (101) crystal plane. The main peak of magnesium hydroxide can be seen from the XRD results (FIG. 3). The XPS results showed that a conversion of the Mg—Mg bond to the Mg—OH bond occurred as the treatment time increased (FIG. 4). The above results indicate that a dense magnesium hydroxide nanosheet layer can be obtained through in situ growth by 12 hours of hydrothermal reaction.

Example 3

Figure 5:
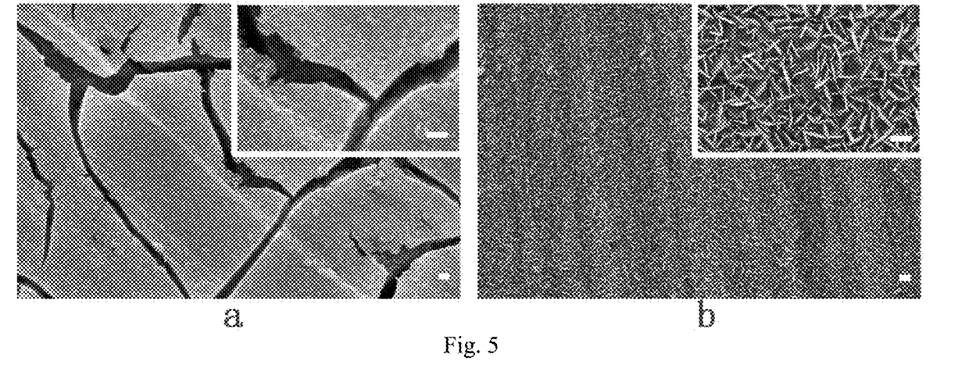
FIG. 5 shows the micromorphology of the sample surface after 3 hours of immersion (scale=1 μm); wherein a represents the untreated magnesium alloy; and b represents HT12.
Figure 6:
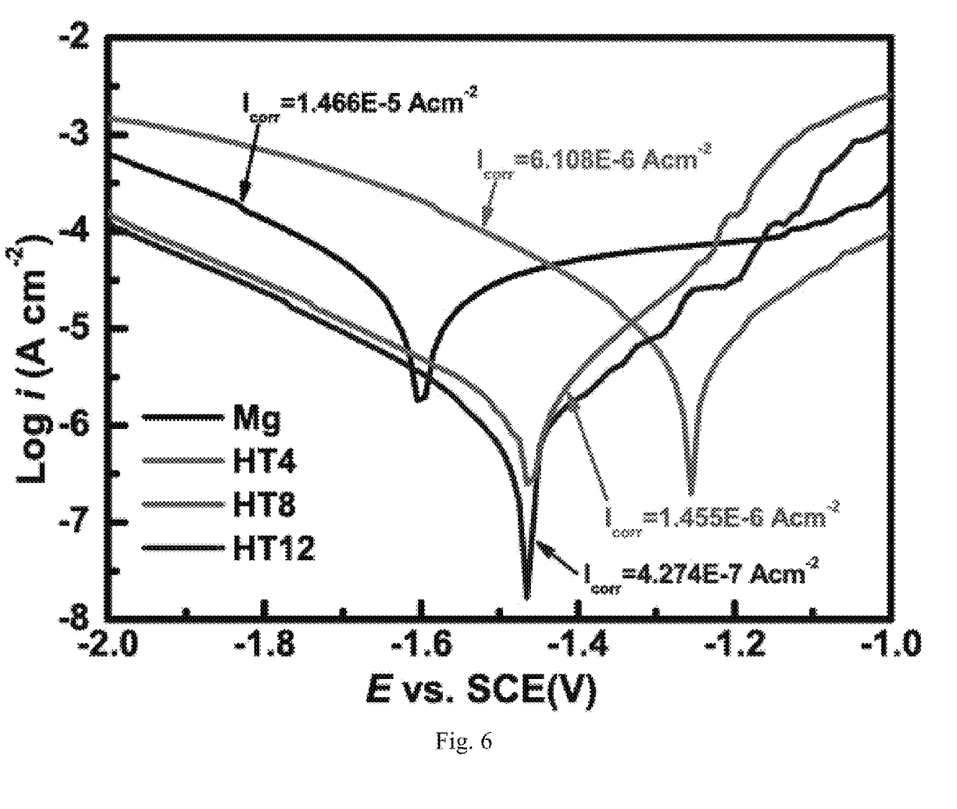
FIG. 6 shows the polarization curves for various samples.
Figure 7:
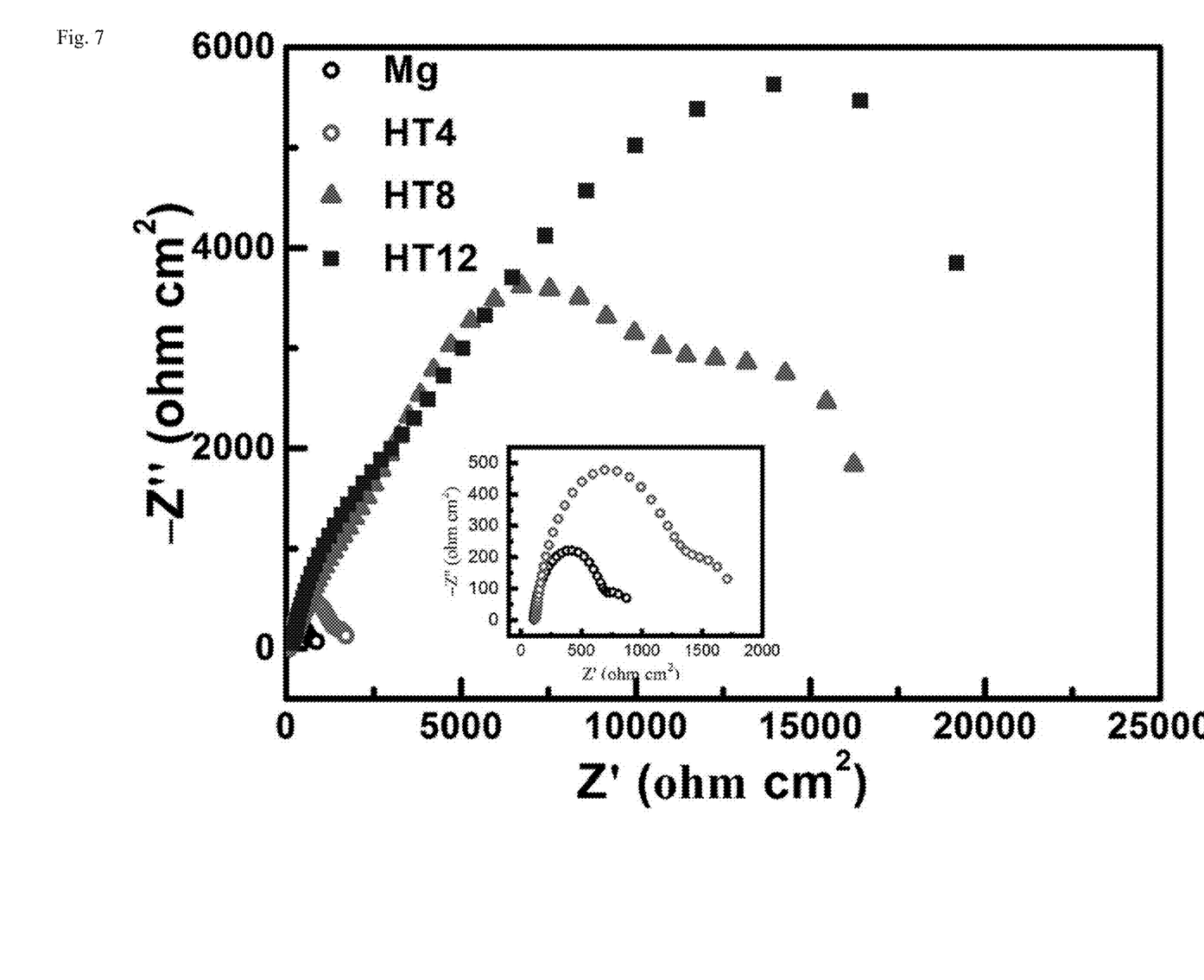
FIG. 7 shows the impedance spectroscopies of various samples.

The corrosion resistance property of the samples was analyzed by an immersion method and an electrochemical analysis method. After immersion of the untreated magnesium block, there were many cracks on the surface, but the surface of the magnesium alloy modified by the magnesium hydroxide sheet layer had no change in structure (FIG. 5). The weight loss analysis showed that the weight loss of the magnesium alloy modified by the nanosheet was significantly reduced compared with that of the magnesium block. The polarization curves showed that as the hydrothermal reaction time increased, the corrosion current gradually decreased (FIG. 6). The impedance spectroscopy showed that the longer the hydrothermal reaction time, the greater the impedance (FIG. 7).

Example 4

Figure 8:
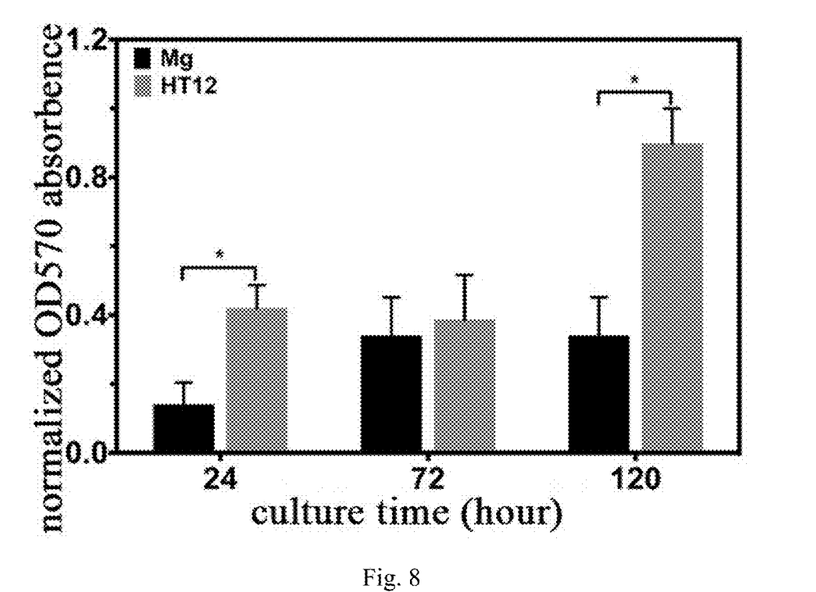
FIG. 8 shows the analysis of biocompatibility.

The samples obtained in Example 1 were sterilized and osteoblasts were cultured on the surface. The proliferation of the cells was examined by MTT. The results showed that the cell proliferation with HT12 was more evident (FIG. 8). It showed that the biocompatibility of the magnesium alloy after 12 hours of hydrothermal treatment was significantly improved compared with that of the untreated magnesium block.

Example 5

Figure 9:
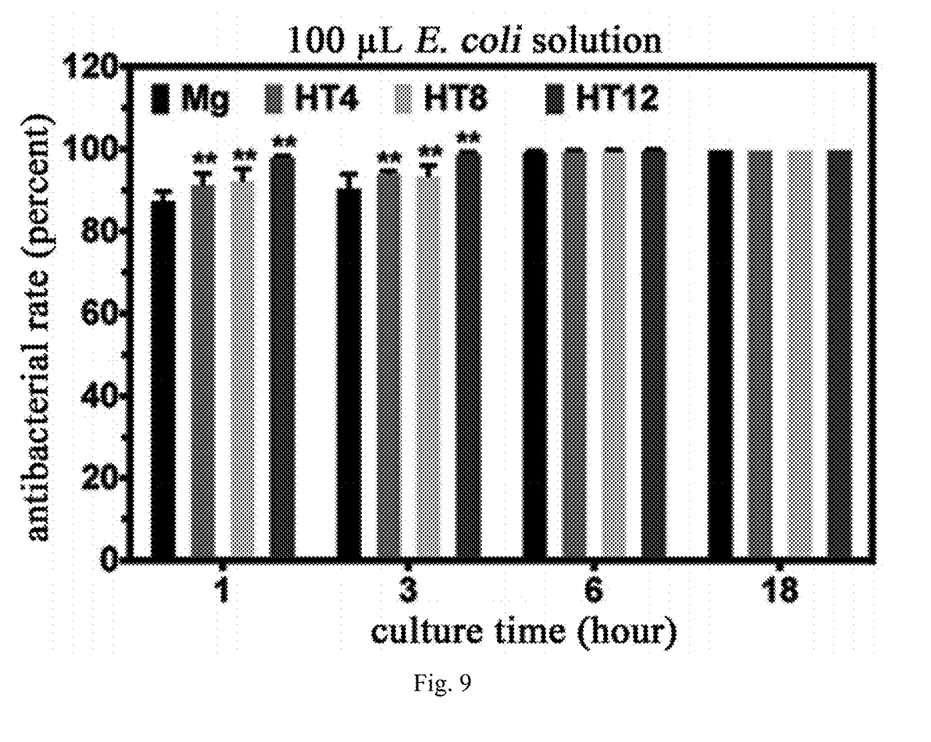
FIG. 9 shows the antibacterial rates against *Escherichia coli* in a 100 μL system.
Figure 10:
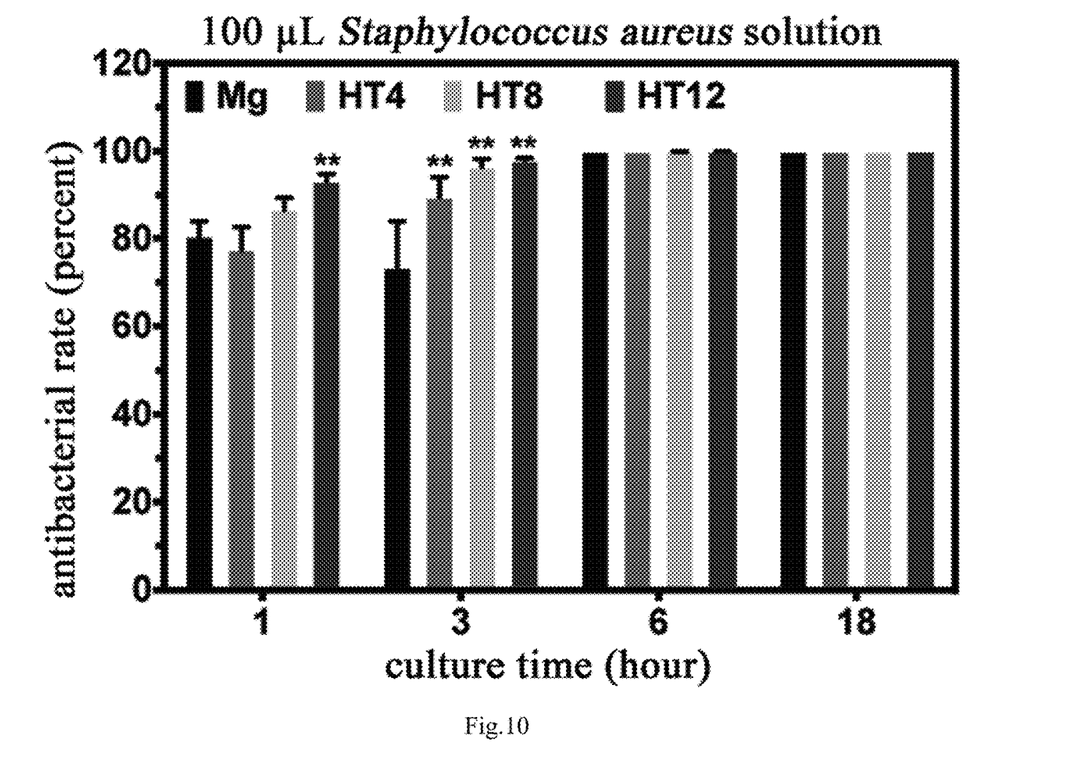
FIG. 10 shows the antibacterial rates against *Staphylococcus aureus* in a 100 μL system.
Figure 11:
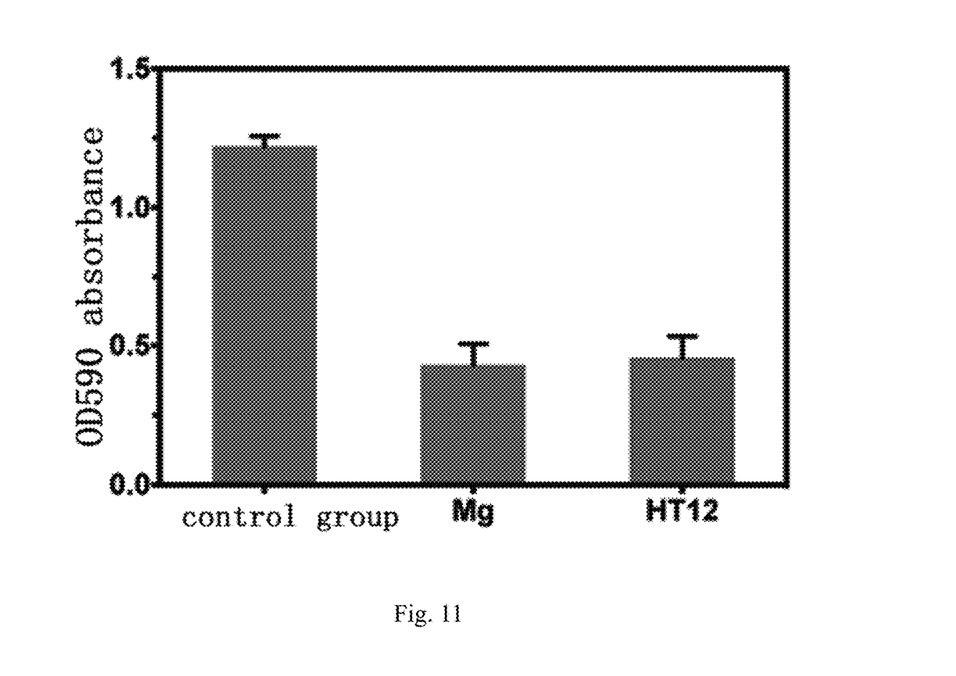
FIG. 11 shows the detection of anti-biofilms.

The samples obtained in Example 1 were used in the antibacterial (*Staphylococcus aureus* and *Escherichia coli*) test. The antibacterial effect was evaluated by the spread plate and count method, and the results were shown in FIG. 9 and FIG. 10. A bactericidal rate of 90% could be achieved for both bacteria by treating for 1 h in a 100 μL system (bacterial concentration being 10$^5$ mL$^{-1}$), and 100% antibacterial rate could be achieved as the treatment time was prolonged to 6 hours (FIG. 9). By increasing the initial colony concentration to be 10 times larger and culturing for 24 hours, the dead bacteria were evidently detected and no continuous biofilm was formed, indicating that HT12 can still effectively inhibit the formation of biofilm (FIG. 11).

Example 6

Figure 12:
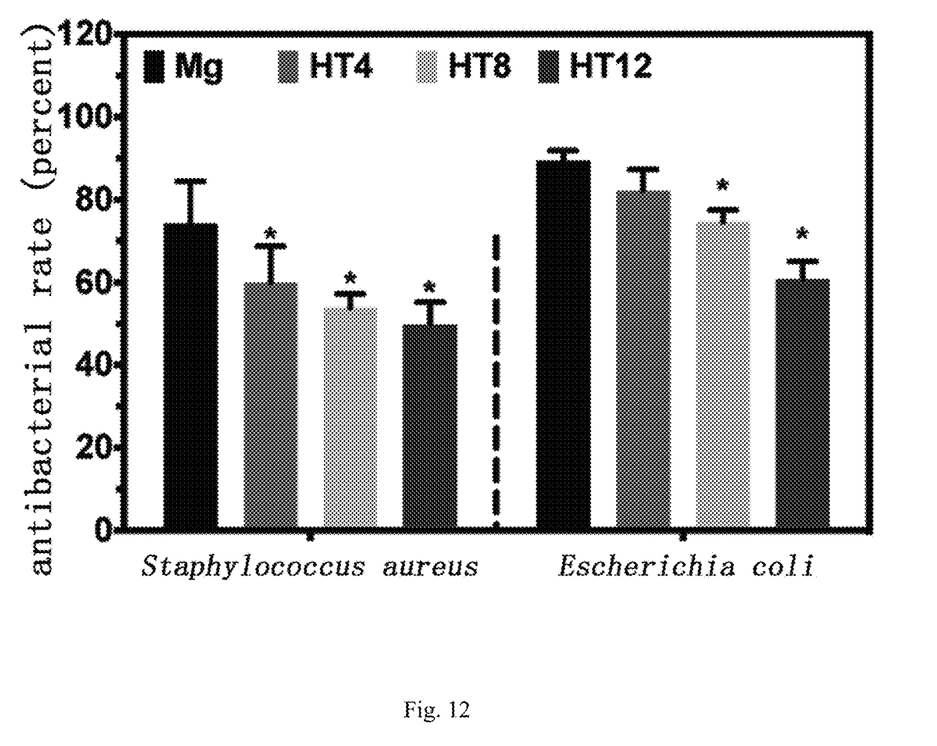
FIG. 12 shows the test of antibacterial effect in a 1 mL system.
Figure 13:
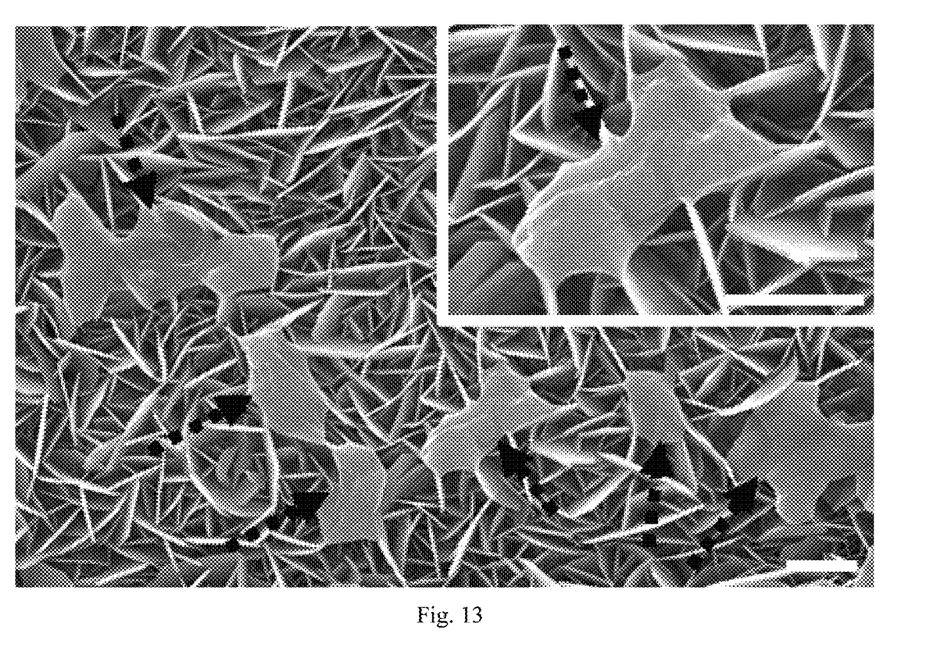
FIG. 13 shows the treated *Escherichia coli* under a scanning electron microscope (scale=1 μm).
Figure 14:
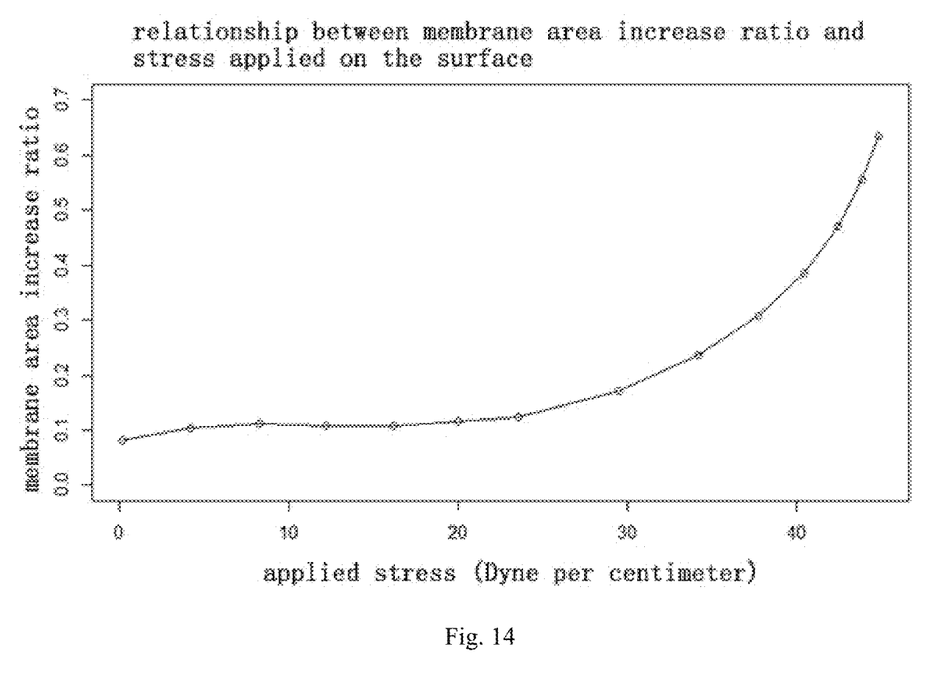
FIG. 14 shows the computer-simulated interaction between bacteria and the materials.
Figure 15A:
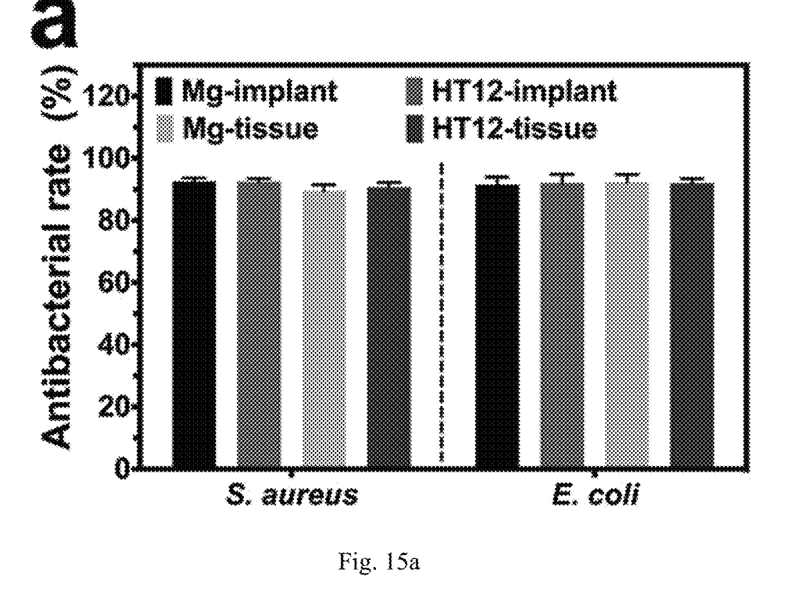
FIG. 15*a* represents the antibacterial results 3 days after the implantation (wherein 'implant' indicates the results at the implant; 'tissue' indicates the results at the surrounding tissues)
Figure 15B:
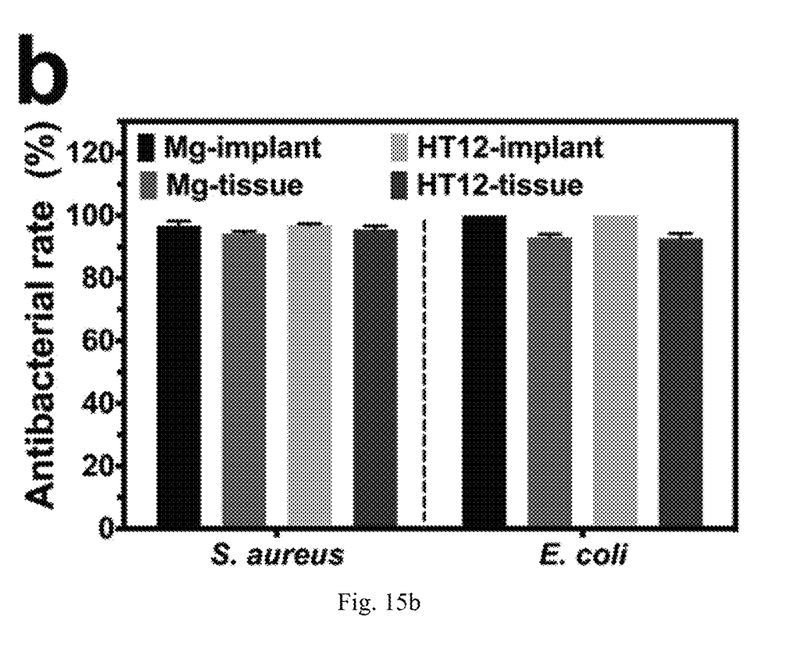
FIG. 15*b* represents the antibacterial results 7 days after the implantation.
Figure 15C:
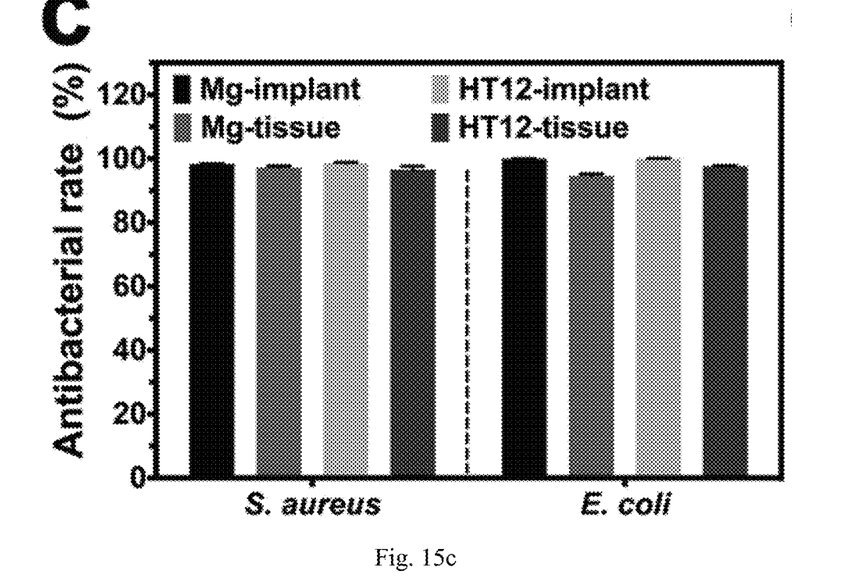
FIG. 15*c* represents the antibacterial results 10 days after the implantation.
Figure 15D:
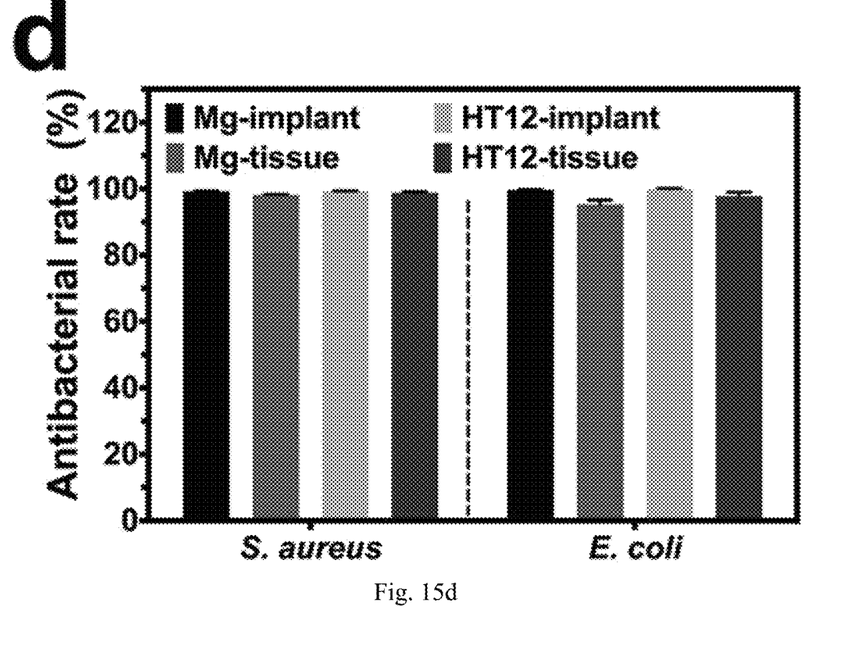
FIG. 15*d* represents the antibacterial results 14 days after the implantation.
Figure 15E:
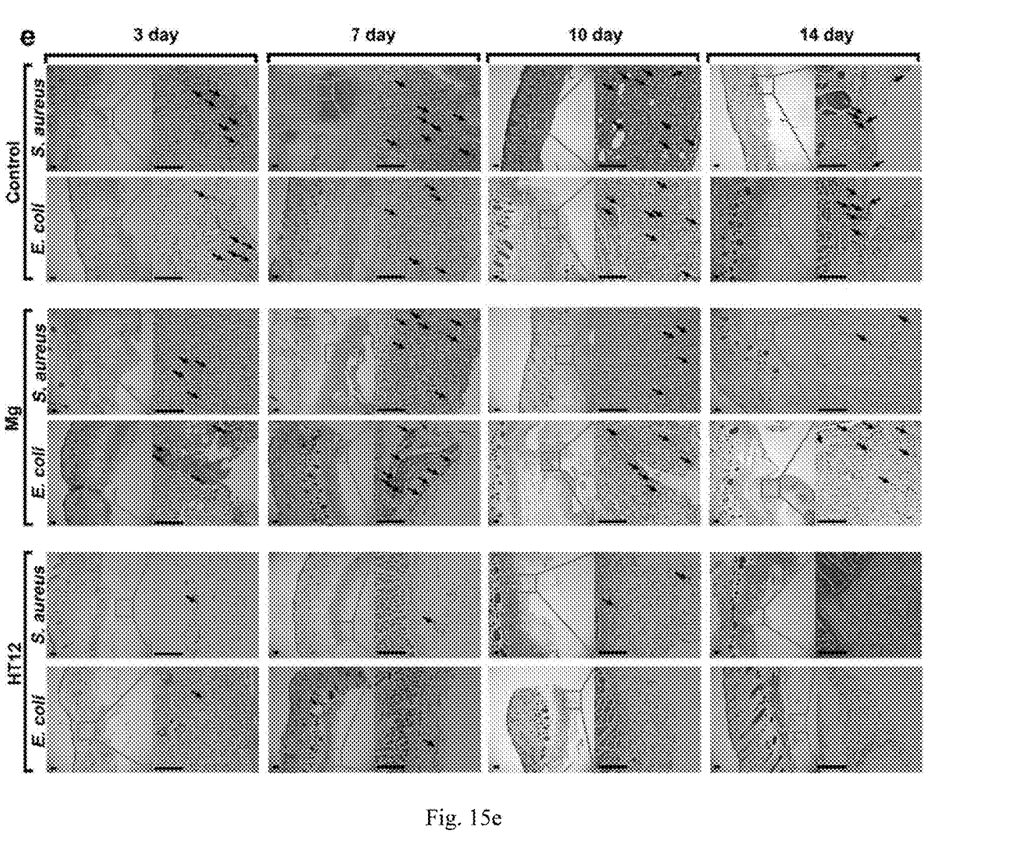
FIG. 15*e* represents the anti-inflammatory results 3-14 days after the implantation (scale=200 μm).

By increasing the volume of the antibacterial system to 1 mL, it was found that the antibacterial effect of HT12 decreased significantly and the group of magnesium block did not change significantly (FIG. 12), indicating that the antibacterial effect of the samples after hydrothermal treatment depends on the surface contact, suggesting that this may be a non-release type antibacterial process. Morphological observation of the treated bacteria by scanning electron microscopy showed that the cell membrane of *Escherichia coli* after HT12 treatment was significantly stretched (FIG. 13). A molecular dynamics model was established to simulate the physical interaction between the bacteria and the interface. It showed that the shear force applied to the bacterial surface could cause the bacterial membrane to be stretched and the membrane area to be increased. When the shear force was 40.5 dyn cm$^{-1}$, the collapse of bacterial membrane appeared, suggesting that the bacterial cell membrane was torn (FIG. 14).

Example 7

The samples of Example 1 were implanted into the subcutaneous tissues of mice as implants, and the untreated magnesium blocks and titanium blocks were used as the control groups. The wounds were carefully sutured after implantation. The implants were taken out on the 3rd, 7th, 10th, and 14th days to detect the bacterial contents at the implant and at surrounding tissues by the spread plate and count method. At the same time, the tissues surrounding the implants were fixed and sliced for H&E staining to verify the effect. The results showed that HT12 can effectively kill the bacteria at the implants and at their surrounding environment. In addition, the inflammatory response of the tissue in the HT12 group was weaker compared with the two control groups (FIGS. 15a-e). These preliminarily demonstrated the feasibility of HT12 as an implant.

What is claimed is:

1. A preparation method of a magnesium alloy material, wherein the preparation method comprises the step of conducting a hydrothermal reaction of a magnesium alloy under an alkaline condition to form a magnesium hydroxide nanosheet layer in situ;
wherein a temperature of the hydrothermal reaction is from 60 to 200° C.; a reaction time of the hydrothermal reaction is more than 30 minutes; and a heating rate of the hydrothermal reaction is 1-30° C.·min$^{-1}$;
wherein the magnesium alloy material comprises a magnesium alloy body and a magnesium hydroxide nanosheet layer on the surface; the magnesium hydroxide nanosheet in the magnesium hydroxide nanosheet layer has an area between 1 nm$^2$ and 10 µm$^2$ and a thickness between 1 nm and 1 µm;
wherein the magnesium alloy body is a magnesium alloy having a magnesium content greater than 85 wt %.

2. The preparation method according to claim 1, wherein the temperature of the hydrothermal reaction is from 80 to 180° C.; the reaction time is more than 2 hours.

3. The preparation method according to claim 1, wherein the alkaline condition refers to a pH value between 8 and 14.

4. The preparation method according to claim 3, wherein the pH value of the hydrothermal reaction is controlled using an aqueous solution of sodium hydroxide, potassium hydroxide, calcium hydroxide, barium hydroxide or aqueous ammonia.

5. The preparation method according to claim 1, wherein the magnesium hydroxide nanosheet has the area between 50 nm$^2$ and 5 µm$^2$ and the thickness between 5 nm and 1 µm.

6. The preparation method according to claim 1, wherein the magnesium alloy body is a magnesium alloy having a magnesium content greater than 90 wt %.

7. The preparation method according to claim 1, wherein the magnesium alloy body is a magnesium alloy having a magnesium content greater than 92 wt %.

8. The preparation method according to claim 1, wherein the temperature of the hydrothermal reaction is from 90 to 160° C.; the reaction time is between 4 and 72 hours.

9. The preparation method according to claim 1, wherein the heating rate of the hydrothermal reaction is 2-20° C.·min$^{-1}$.

10. The preparation method according to claim 1, wherein the alkaline condition refers to a pH value between 8 and 12.

* * * * *